(12) United States Patent
Papac et al.

(10) Patent No.: US 8,449,147 B2
(45) Date of Patent: May 28, 2013

(54) OPHTHALMIC ENDOILLUMINATION WITH THERMALLY ISOLATED PHOSPHOR

(75) Inventors: Michael James Papac, Tustin, CA (US); Christopher Horvath, Irvine, CA (US); Ronald T. Smith, Irvine, CA (US); Michael J. Yadlowsky, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 537 days.

(21) Appl. No.: 12/852,758

(22) Filed: Aug. 9, 2010

(65) Prior Publication Data

US 2011/0037949 A1    Feb. 17, 2011

Related U.S. Application Data

(60) Provisional application No. 61/233,388, filed on Aug. 12, 2009.

(51) Int. Cl.
*F21V 29/00* (2006.01)
*H01J 1/62* (2006.01)

(52) U.S. Cl.
USPC ............................. 362/294; 313/512; 362/373

(58) Field of Classification Search
USPC ........................... 362/294, 373; 313/512, 310
See application file for complete search history.

(56) References Cited

U.S. PATENT DOCUMENTS

2004/0150312 A1*  8/2004  McElrath et al. ............ 313/310
2009/0059359 A1   3/2009  Nahm et al.

FOREIGN PATENT DOCUMENTS

EP        0305170        3/1989
WO    WO 2009/005763    1/2009

OTHER PUBLICATIONS

International Search Report for PCT/US2010/044911, 4 pages.
Written Opinion of the International Searching Authority, International Application No. PCT/US2010/044911, 6 pages.

* cited by examiner

*Primary Examiner* — Joseph L Williams
(74) *Attorney, Agent, or Firm* — Keiko Ichiye

(57) ABSTRACT

An illuminator configured to deliver white light into an optical fiber includes a pump light source and a white phosphor. The pump light source configured to emit short-wavelength light. The white phosphor is disposed to receive the short-wavelength light from the pump light source and to output white light in response to the pumping light. The white phosphor is thermally isolated from the pump light source.

10 Claims, 3 Drawing Sheets

_(US 8,449,147 B2)_

OPHTHALMIC ENDOILLUMINATION WITH THERMALLY ISOLATED PHOSPHOR

RELATED APPLICATIONS

This application claims priority to U.S. provisional application Ser. No. 61/233,388, filed on Aug. 12, 2009, the contents which are incorporated herein by reference.

TECHNICAL FIELD OF THE INVENTION

The present invention relates to an illuminator for use in ophthalmic surgery and more particularly to an ophthalmic endoilluminator to produce a light suitable for illuminating the inside of an eye.

BACKGROUND OF THE INVENTION

Anatomically, the eye is divided into two distinct parts—the anterior segment and the posterior segment. The anterior segment includes the lens and extends from the outermost layer of the cornea (the corneal endothelium) to the posterior of the lens capsule. The posterior segment includes the portion of the eye behind the lens capsule. The posterior segment extends from the anterior hyaloid face to the retina, with which the posterior hyaloid face of the vitreous body is in direct contact. The posterior segment is much larger than the anterior segment.

The posterior segment includes the vitreous body—a clear, colorless, gel-like substance. It makes up approximately two-thirds of the eye's volume, giving it form and shape before birth. It is composed of 1% collagen and sodium hyaluronate and 99% water. The anterior boundary of the vitreous body is the anterior hyaloid face, which touches the posterior capsule of the lens, while the posterior hyaloid face forms its posterior boundary, and is in contact with the retina. The vitreous body is not free-flowing like the aqueous humor and has normal anatomic attachment sites. One of these sites is the vitreous base, which is a 3-4 mm wide band that overlies the ora serrata. The optic nerve head, macula lutea, and vascular arcade are also sites of attachment. The vitreous body's major functions are to hold the retina in place, maintain the integrity and shape of the globe, absorb shock due to movement, and to give support for the lens posteriorly. In contrast to aqueous humor, the vitreous body is not continuously replaced. The vitreous body becomes more fluid with age in a process known as syneresis. Syneresis results in shrinkage of the vitreous body, which can exert pressure or traction on its normal attachment sites. If enough traction is applied, the vitreous body may pull itself from its retinal attachment and create a retinal tear or hole.

Various surgical procedures, called vitreo-retinal procedures, are commonly performed in the posterior segment of the eye. Vitreo-retinal procedures are appropriate to treat many serious conditions of the posterior segment. Vitreo-retinal procedures treat conditions such as age-related macular degeneration (AMD), diabetic retinopathy and diabetic vitreous hemorrhage, macular hole, retinal detachment, epiretinal membrane, CMV retinitis, and many other ophthalmic conditions.

A surgeon performs vitreo-retinal procedures with a microscope and special lenses designed to provide a clear image of the posterior segment. Several tiny incisions just a millimeter or so in length are made on the sclera at the pars plana. The surgeon inserts microsurgical instruments through the incisions such as a fiber optic light source to illuminate inside the eye, an infusion line to maintain the eye's shape during surgery, and instruments to cut and remove the vitreous body.

During such surgical procedures, proper illumination of the inside of the eye is important. Typically, a thin optical fiber is inserted into the eye to provide the illumination. A light source, such as a metal halide lamp, a halogen lamp, a xenon lamp, or a mercury vapor lamp, is often used to produce the light carried by the optical fiber into the eye. The light passes through several optical elements (typically lenses, mirrors, and attenuators) and is emitted to the optical fiber that carries the light into the eye. The quality of this light is dependent on several factors including the types of optical elements selected.

SUMMARY OF THE INVENTION

An illuminator configured to deliver white light into an optical fiber includes a pump light source and a white phosphor. The pump light source configured to emit short-wavelength light. The white phosphor is disposed to receive the short-wavelength light from the pump light source and to output white light in response to the pumping light. The white phosphor is thermally isolated from the pump light source.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DESCRIPTION OF THE INVENTION

Preferred embodiments of the present invention are illustrated in the Figures, like numerals being used to refer to like and corresponding parts of the various drawings.

Figure 1:
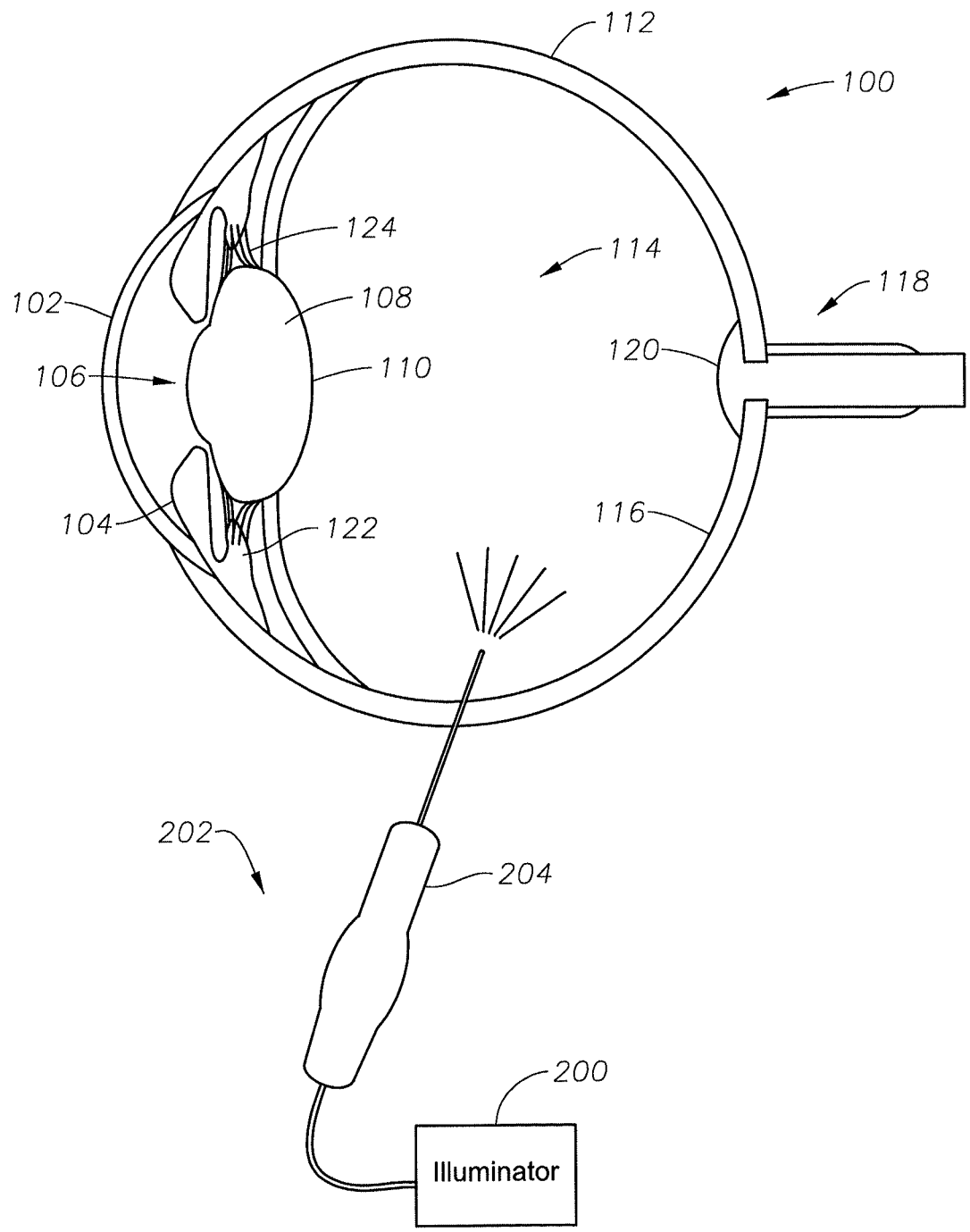
FIG. 1 illustrates the anatomy of the eye in which an ophthalmic endoilluminator in accordance with embodiments of the present invention may be placed.

FIG. 1 illustrates the anatomy of the eye into which the improved design for ocular implant provided by the present invention may be placed. Eye 100 includes cornea 102, iris 104, pupil 106, lens 108, lens capsule 110, zonules, ciliary body 120, sclera 112, vitreous gel 114, retina 116, macula, and optic nerve 120. Cornea 102 is a clear, dome-shaped structure on the surface of the eye acts as a window, letting light into the eye. Iris 104 is the colored part of the eye, called the iris, is a muscle surrounding the pupil that relaxes and contracts to control the amount of light entering the eye. Pupil 106 is the round, central opening of the iris. Lens 108 is the structure inside the eye that helps to focus light on the retina. Lens capsule 110 is an elastic bag that envelops the lens, helping to control lens shape when the eye focuses on objects at different distances. Zonules are slender ligaments that attach the lens capsule to the inside of the eye, holding the lens in place. The ciliary body is the muscular area attached to the lens that contracts and relaxes to control the size of the lens for focusing. Sclera 112 is the tough, outermost layer of the eye that maintains the shape of the eye. Vitreous gel 114 is the large, gel-filled section that is located towards the back of the eyeball, and which helps to maintain the curvature of the eye. Retina 116 is a light-sensitive nerve layer in the back of the eye that receives light and converts it into signals to send to the brain. The macula is the area in the back of the eye that contains receptors for seeing fine detail. Optic nerve 118 connects and transmits signals from the eye to the brain.

Ciliary body 122 lies just behind the iris 104. Attached to the ciliary body 122 are tiny fiber "guide wires" called zonules 124. Lens 108 is suspended inside the eye by the zonular fibers 124. Nourishment for the ciliary body 122 comes from blood vessels which also supply the iris 104. One function of ciliary body 122 is to control accommodation by changing the shape of the lens 108. When the ciliary body 122 contracts, the zonules 124 relax. This allows the lens 108 to thicken, increasing the eye's ability to focus up close. When looking at a distant object, ciliary body 122 relaxes, causing the zonules 124 to contract. The lens 108 then becomes thinner, adjusting the eye's focus for distance vision.

FIG. 1 also shows a cross sectional view of an ophthalmic endoilluminator 200, which may be an endoilluminator according to various embodiments of the present invention, located in an eye. FIG. 1 depicts illuminator 200 coupled by an optical fiber to a handpiece 202 with probe 204 in use. Probe 204 is inserted into eye 100 through an incision in the pars plana region. Probe 204 illuminates the inside or vitreous region 114 of eye 100. In this configuration, probe 204 can be used to illuminate the inside or vitreous region 114 during vitreo-retinal surgery.

Ophthalmic endoilluminators have been previously based either on halogen tungsten lamps or high pressure arc lamps (metal-halides, Xe). The advantages of arc lamps are small emitting area (<1 mm), color temperature close to daylight, and longer life than in halogen lamps—400 hours vs. 50 hours. The disadvantage of arc lamps is high cost, decline in power, complexity of the systems and the need to exchange lamps several times over the life of the system.

LED based illuminators may provide considerably lower cost and complexity, and characteristic life times of 50,000 to 100,000 hours that would allow operating ophthalmic fiber illuminator for entire life of the instrument with very little drop in output and without a need of exchanging LEDs. A typical white LED may include a short-wavelength (ultra violet (UV)/violet/blue) LED exciting a white phosphor cap that emits white light, the source of light exciting the white phosphor layer being referred to as a "pump light source." One limit to the output brightness of the white LED is that the quantum efficiency of the white phosphor, i.e., the number of photons emitted per photon incident on the phosphor material, depends on the temperature of the phosphor material. Specifically, as the temperature of the phosphor material increases, the quantum efficiency decreases. One significant drawback of existing systems is that the short-wavelength LED must operate at a relatively high temperature in order to produce sufficiently bright short-wavelength light for an adequate output brightness of the white phosphor. But this in turn limits the efficiency of the white phosphor layer.

Unlike conventional illuminators, various embodiments of the present invention thermally isolate the white phosphor from the short-wavelength LED. For purposes of this specification, "white phosphor" refers not only to broad band white phosphor materials but also to wavelength converting materials that either combine with light from the pump light source or combine light of different colors from multiple materials to produce bright light in a relatively broad region of the visible spectrum. For purposes of this specification, "thermally isolated" means that heat from the pump light source is either prevented from conducting directly to the white phosphor layer by the use of intervening insulators, heat sinks, air gaps, or other techniques known in the art or conducted away in a sufficient amount that the temperature of the white phosphor layer is primarily determined by the equilibrium temperature of another structure than the pump light source. Because the white phosphor is thermally isolated from the short-wavelength pump light source, the quantum efficiency of the white phosphor can be preserved even when the short-wavelength pump light source operates at a relatively high efficiency. While conventional illuminators would suggest that the intimate contact of the short-wavelength LED to the white phosphor is necessary for adequate incidence of short-wavelength light on the white phosphor, various embodiments of the present invention have demonstrated that allowing thermal isolation between the short-wavelength LED and the white phosphor can allow for sufficiently increased quantum efficiency to produce greater brightness even given the additional complications involved in thermally isolating the components.

Figure 2:
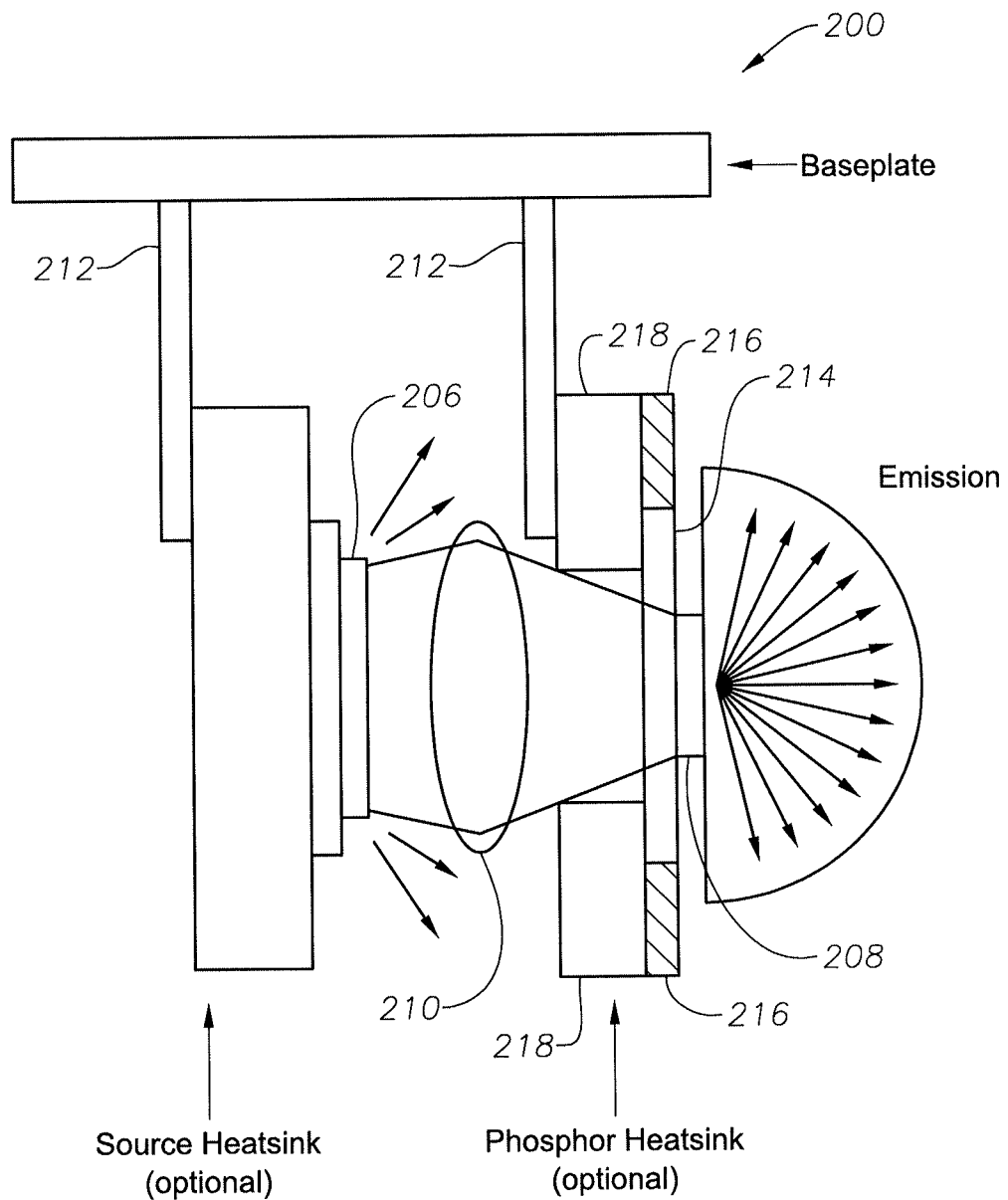
FIG. 2 illustrates in more detail an illuminator according to a particular embodiment of the present invention.

FIG. 2 illustrates a particular embodiment of the illuminator 200 in greater detail. In the illustrated embodiment, illuminator 200 includes a pump light source 206 separated from a white phosphor 208 by a light collector 210. The pump light source 206 and white phosphor 208 are held at a distance from one another by thermally insulating mounts 212, so that the pump light source 206 and white phosphor 208 are thermally isolated from one another. The light collector 210 helps to compensate for the increased separation by collecting light emitted by the pump light source 206 and directing it onto the white phosphor 208.

The white phosphor 208 is mounted on a substrate 214 of material transparent to the short-wavelength light of the pump light source 206. A base of the substrate 214 is connected to the thermally insulating mount 212 by a thermoelectric cooler 216 and a cooling plate 218. The cooling plate 218 provides additional mass to take up heat that can be conducted, convected, or radiated away, which may advantageously be formed from a thermally conductive material such as a metal. The thermoelectric cooler 216 is an electrical heat pump that is commonly used as an active cooling device for semiconductors and in this case is used to remove heat from the white phosphor 208. Although the specific example of a thermoelectric cooler 216 is illustrated, it should be understood that any sort of active or passive cooling device suitable for use in relatively small spaces could be used, including liquid or air cooling systems. More generally, any type of "heat sink," referring to any combination of elements or materials that actively or passively remove sufficient heat from the white phosphor 208 so as to primarily determine the temperature of the white phosphor 208 as compared to the pump light source 206, may be employed to assist in thermally isolating the white phosphor 208

Figure 3:
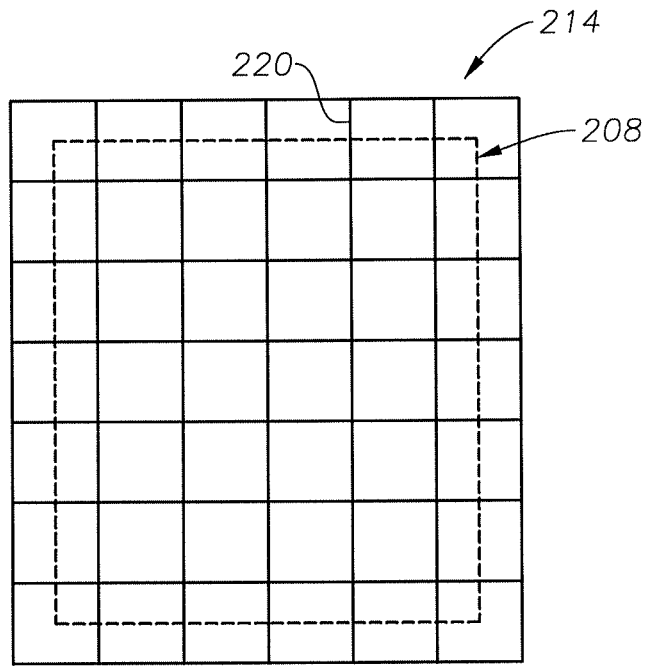
FIG. 3 illustrates a substrate for a white phosphor according to a particular embodiment of the present invention.

FIG. 3 illustrates a particular embodiment of the present invention using a substrate 214 that includes a thermally conductive material 220. The conductive material 220 may be any suitable material with a higher thermal conductivity than the substrate 214, including but not limited to metals such as copper or carbon nanotubes. Liquid and/or thermoelectric cooling may also be used in conjunction with conductive material 220. In the depicted embodiment, the conductive material 220 is formed into a grid covering an area substantially equal to the area of a back surface of the white phosphor 208 facing the substrate 214. This advantageously increases the thermal contact area with the white phosphor 208 in order to provide more efficient cooling.

Figure 4A:
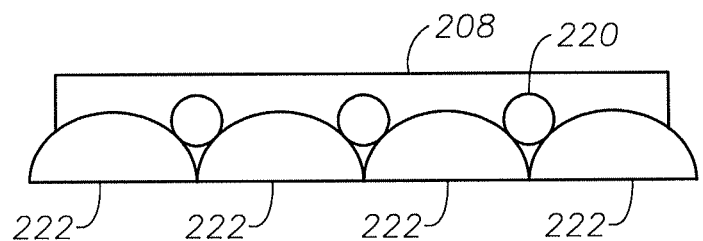
FIGS. 4A and 4B illustrate optical elements used to direct light around an opaque conductive material according to particular embodiments of the present invention.
Figure 4B:
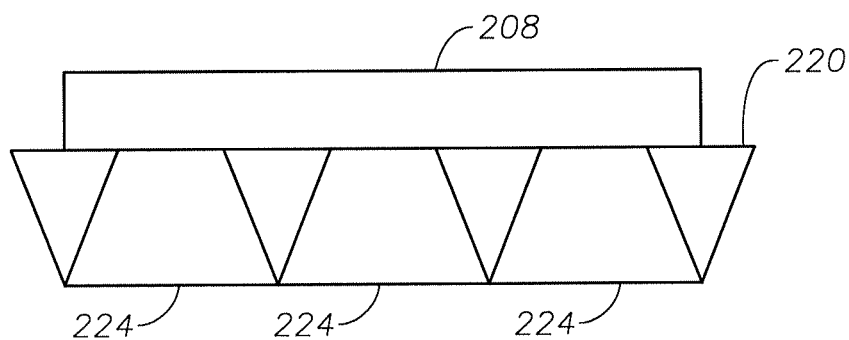

In principle, conductive material 220 may be transparent to short-wavelength light from the pump light source 206, but many materials that are desirable in terms of having a high thermal conductivity are opaque. The use of such materials can cause loss of light incident on the white phosphor 208 due to shadowing of the white phosphor 208 by the opaque conductive material 220. FIGS. 4A and 4B illustrate embodiments of the substrate 214 that can help to prevent light loss from absorption by the opaque conductive material 220. In FIG. 4A, the substrate 214 includes a plurality of lenses 222 having planar back surfaces. The planar back surfaces of the lenses 222 extend across the back surface of the substrate 214 so as to allow light to be collected across substantially the entire back surface. The lenses 222 then focus the light into gaps between the conductive material 220, so that light hitting the back surface of the substrate 214 does not hit the conductive material 220. FIG. 4B illustrates a similar configuration of the substrate 214 in which lenses 224 are placed between conductive material 220. In FIG. 4B, the conductive material 220 has a wider cross-sectional area near the white phosphor 208 to improve the thermal contact area and to make cooling of the white phosphor 208 more efficient. Conversely, the lenses 224 have a wider cross-sectional area facing the pump light source 206 at the back surface of the substrate 214, allowing light to be collected over a wider area and to be directed between gaps in the conductive material 220.

The present invention is illustrated herein by example, and various modifications may be made by a person of ordinary skill in the art. Although the present invention is described in detail, it should be understood that various changes, substitutions and alterations can be made hereto without departing from the scope of the invention as claimed.

What is claimed is:

1. An illuminator configured to deliver white light into an optical fiber, comprising:
    a pump light source configured to emit short-wavelength light;
    a white phosphor disposed to receive the short-wavelength light from the pump light source and to output white light in response to the pumping light, wherein the white phosphor is thermally isolated from the pump light source; and
    a heat sink thermally coupled to the white phosphor, the heat sink comprising a grid of conductive material covering an area greater than or substantially equal to that of a surface of the white phosphor facing the grid.

2. The illuminator of claim 1, wherein the pump light source comprises a light-emitting semiconductor junction.

3. The illuminator of claim 1, wherein the short-wavelength light is ultraviolet light.

4. The illuminator of claim 1, wherein the white phosphor is formed from YAG:Ce.

5. The illuminator of claim 1, wherein the heat sink comprises carbon nanotubes.

6. The illuminator of claim 1, wherein the heat sink comprises at least one active cooling device.

7. An illuminator configured to deliver white light into an optical fiber, comprising:
    a pump light source configured to emit short-wavelength light;
    a white phosphor disposed to receive the short-wavelength light from the pump light source and to output white light in response to the pumping light, the white phosphor thermally isolated from the pump light source;
    a heat sink thermally coupled to the white phosphor; and
    at least one optical element configured to redirect the short-wavelength light around the heat sink to the white phosphor.

8. An illuminator configured to deliver white light into an optical fiber, comprising:
    a pump light source configured to emit short-wavelength light;
    a white phosphor disposed to receive the short-wavelength light from the pump light source and to output white light in response to the pumping light, the white phosphor thermally isolated from the pump light source, the white phosphor deposited in a layer on a substrate; and
    a heat sink thermally coupled to the white phosphor, the heat sink comprising a thermally conductive material within the substrate.

9. An illuminator configured to deliver white light into an optical fiber, comprising:
    a pump light source configured to emit short-wavelength light; and
    a white phosphor disposed to receive the short-wavelength light from the pump light source and to output white light in response to the pumping light, the white phosphor thermally isolated from the pump light source, the pump light source and the white phosphor mounted spaced from one another by thermally insulating mounts.

10. The illuminator of claim 9, further comprising a light collector between the pump light source and the white phosphor.

* * * * *